United States Patent [19]

Rabenhorst et al.

[11] Patent Number: 5,017,388

[45] Date of Patent: May 21, 1991

[54] PROCESS FOR THE PREPARATION OF VANILLIN

[75] Inventors: Jürgen Rabenhorst, Bevern; Rudolf Hopp, Holzminden, both of Fed. Rep. of Germany

[73] Assignee: Haarmann & Reimer GmbH, Holzminden, Fed. Rep. of Germany

[21] Appl. No.: 533,601

[22] Filed: Jun. 5, 1990

[30] Foreign Application Priority Data

Jun. 20, 1989 [DE] Fed. Rep. of Germany ....... 3920039

[51] Int. Cl.$^5$ ............................................. A23L 1/221
[52] U.S. Cl. ...................................... 426/44; 426/52; 426/650; 426/655
[58] Field of Search ....................... 426/7, 52, 61, 650, 426/655, 44

[56] References Cited

U.S. PATENT DOCUMENTS 2,621,127 12/1952 Towt ...................................... 426/44
2,835,591 5/1958 Graves et al. .......................... 426/44
3,352,690 11/1967 Kaul ....................................... 426/44
4,874,701 10/1989 Cooper ................................. 435/147

FOREIGN PATENT DOCUMENTS 3604874 8/1987 Fed. Rep. of Germany.
0812443 4/1959 United Kingdom ................. 426/44

OTHER PUBLICATIONS

Agricultural and Biological Chemistry, vol. 47, Sep. 1983, K. Tadasa et al., Initial Steps of Eugenol Degradation Pathway of a Microorganism, pp. 2639–2640.
Agricultural and Biological Chemistry, vol. 41, Jun. 1977, K. Tadasa, Degradation of Eugenol by a Microorganism, pp. 926–929.

*Primary Examiner*—Marianne Cintins
*Attorney, Agent, or Firm*—Sprung, Horn, Kramer & Woods

[57] ABSTRACT

A process for the preparation of natural vanillin is disclosed wherein eugenol and/or isoeugenol is oxidized microbially to vanillin using microorganisms of the genera Serratia, Klebsiella or Enterobacter.

5 Claims, No Drawings

PROCESS FOR THE PREPARATION OF VANILLIN

The invention relates to a process for the preparation of natural vanillin by fermentative oxidation of eugenol and/or isoeugenol.

Vanillin is an important flavoring which is much used in the foodstuff and luxury food industry. Hitherto it is mainly prepared from the lignin of sulfite waste liquors, and occasionally by chemical means by oxidation of eugenol or isoeugenol. However, the vanillin obtained in this way has the disadvantage that it is not a natural substance within the meaning of foodstuffs legislation and therefore may not be called a natural flavoring either.

The natural flavoring vanillin is to date obtainable only by extraction from vanilla pods; however, the natural vanillin obtained in this way is much too costly for use on an industrial scale.

It is disclosed in Agric. Biol. Chem. 41, 925–929 (1977) and 74, 2639–2640 (1983) that eugenol provides, on microbial breakdown by bacteria of the genus Corynebacterium sp. and Pseudomonas sp., vanillin in addition to ferulic acid, coniferyl alcohol, coniferyl aldehyde and vanillic acid. However, this breakdown cannot be used for the preparation of vanillin from eugenol because the microorganisms are not available as such and, moreover, vanillin is produced in a mixture of substances, from which it can isolated in pure form only with considerable effort.

For isoeugenol, to date only fungi which are able to oxidize isoeugenol to vanillin have been found. In this microbial conversion too, vanillin is produced in a mixture with other compounds because the oxidation goes further to vanillic acid and, moreover, undesired dimerizations of isoeugenol occur (see Bioflavor 87, Ed.: P. Schreier, 399–413 (1988); Bio Engineering 4 (3) 116–117 (1988)). Additional disadvantages are those known to be associated with the fermentation of mycelium-forming fungi, such as relatively slow growth, inhomogeneities in the medium, etc.

In the search for a new preparation process which can be employed in practice for natural vanillin, it has now been found that the latter is obtained in an economic manner in good yields by microbial oxidation of eugenol and/or isoeugenol with the aid of particular, readily obtainable microorganisms.

It has been found, surprisingly, that these particular microorganisms convert not only eugenol but also isoeugenol into vanillin.

Hence the invention relates to a process for the preparation of natural vanillin, which is characterized in that eugenol and/or isoeugenol is oxidized to vanillin using microorganisms of the genera Serratia, Klebsiella or Enterobacter, in particular of strains of Serratia ficaria, Serratia fonticola, Serratia liquefaciens, Serratia marcescens, Serratia marinorubra, Serratia odorifera, Serratia plymuthica, Serratia rubidaea, Enterobacter aerogenes, Enterobacter agglomerans, Enterobacter cloacae, Klebsiella aerogenes, Klebsiella pneumoniae and Klebsiella edwardsii.

Examples of representatives of the microorganisms of the above-mentioned genera to be used according to the invention are the strains deposited at the Deutsche Sammlung fur Mikroorganismen (German Microorganism Collection), Brunswick, with the numbers DSM 49, 1608, 1636, 3264, 30053, 30054, 30063, 30121, 30122, 30124, 30125, 20126 and 30127 or the strains deposited at the ATCC, Rockville, USA, with the numbers ATCC 13 882, 13 883, 13 886, 27593, 27614, 29844, 33077 and 33105 or the strains deposited at the NCTC, London, GB, NCTC 10 912, 11 214, and 12 147, as well as the mutants thereof. Mutants of these strains are obtained by spontaneous or induced mutation. The mutagenesis can be brought about, for example, by UV irradiation or mutagenic substances. The preparation and selection of such mutants are generally known processes.

The process according to the invention is preferably carried out as follows:

Firstly the microorganism to be used according to the invention is cultivated in a customary culture medium in a manner customary for the cultivation of microorganisms. The substrate can be added at the start of incubation, during or after cessation of growth, all at once or distributed over a lengthy period. In this connection, the amount of eugenol or isoeugenol is advantageously regulated such that the concentration of the compounds is 0.2 to 100 g/l of culture broth, preferably 5 to 50 g/l of culture broth. The progress of the oxidation is followed by determining the vanillin content of the culture broth by high-pressure liquid chromatography. Once the optimal amount of vanillin has been produced, the latter is isolated from the culture broth by known physical processes such as extraction, distillation or chromatography. The crude vanillin obtained in this way can be further purified by recrystallization from water.

The microorganisms to be used according to the invention can be cultivated in synthetic, semisynthetic and natural culture media. These culture media contain carbon sources, nitrogen sources and, where appropriate, inorganic salts, trace elements and vitamins.

Examples of carbon sources which can be used are sugars such as D-glucose, sugar alcohols such as glycerol or mannitol, organic acids such as citric acid, or complex mixtures such as malt extract.

Examples of suitable nitrogen sources are inorganic nitrogen sources such as nitrates and ammonium salts and organic nitrogen sources such as yeast extract, soya meals, cottonseed meal, wheat gluten and corn steep liquor.

Inorganic salts which can be used are sulfates, nitrates, chlorides, carbonates and phosphates of sodium, potassium, magnesium, calcium, zinc and iron.

The cultivation temperature is preferably in the range from 15 to 45° C., particularly preferably in the range from 25 to 35° C. The pH of the culture medium is preferably 3 to 9, in particular 3.5 to 7.5. The cultivation can be carried out either in suitable shaking apparatus or in fermenters with stirring devices. Care must be taken that there is sufficient aeration during the cultivation. The cultivation can be carried out batchwise, semicontinuously and continuously. The culture time until a maximum amount of vanillin is reached is between 48 and 300 hours from the start of substrate addition. It may be advantageous, in order to protect the microorganisms from the toxic effect of eugenol or isoeugenol, for adsorbents for the substrates to be added to the culture media, for example active charcoal or adsorber resins such as Amberlite XAD-2, Lewatit OC 1062, Lewatit OC 1064, Amberlite XAD-7 and Amberlite XAD-16.

EXAMPLE 1

Ten 500 ml conical flasks are each charged with 100 ml of a solution of 10 g of glycerol, 3.125 g of $Na_2HPO_4$, 2.5 g of $KH_2PO_4$, 2.5 g of $(NH_4)_2SO_4$, 0.025 g of $FeSO_4 \times 7 H_2O$ in 1000 ml of water and subsequently sterilized at 121° C. for 20 min. Subsequently 0.2 ml of a 1 molar $MgSO_4$ solution and 0.3 ml of a 0.1 molar $CaCl_2$ solution are added to each conical flask which, after cooling, is inoculated with the microorganism Serratia marcescens DSM 30126. The cultures are incubated at 27° C. and 150 rpm on a rotating shaker. After 2 days, 2 g of isoeugenol are added to each of the individual cultures, which are subjected to further rotary shaking at 27° C. After 10 days, the vanillin content in the culture broths is determined by means of HPLC. The vanillin yield is then 900 mg/l corresponding to a yield of about 5% of theory based on isoeugenol employed.

Comparable yields are also obtained on use of the microorganisms *Serratia ficaria, Serratia fonticola, Serratia liquefaciens, Serratia marinorubra, Serratia odorifera, Serratia plymuthica, Serratia rubidaea, Enterobacter aerogenes, Enterobacter agglomerans, Enterobacter cloacae, Klebsiella aerogenes, Klebsiella pneumoniae* and *Klebsiella edwardsii*.

EXAMPLE 2

Ten 500 ml conical flasks are each charged with 100 ml of a solution of 3 g of meat extract, 5 g of meat peptone, 1 g of yeast extract and 1 g of inositol in 1 l of water (pH of the solution: 7) and sterilized at 121° C. for 20 min. After cooling, the flasks are inoculated with the microorganism *Serratia marcescens DSM* 30126 and incubated at 27° C. and 150 rpm on a rotating shaker. After 24 hours, 2 g of eugenol are added to each of the cultures, which are subjected to further rotary shaking at 27° C. After 13 days, the vanillin content in the culture broths, determined by HPLC, is 18 mg/l.

Approximately the same yields are obtained with the microorganisms of the other genera, *Serratia ficaria, Serratia fonticola, Serratia liquefaciens, Serratia marinorubra, Serratia odorifera, Serratia plymuthica, Serratia rubidaea, Enterobacter aerogenes, Enterobacter agglomerans, Enterobacter cloacae, Serratia marinorubra, Serratia odorifera, Serratia rubidaea, Klebsiella aerogenes, Klebsiella pneumoniae* and *Klebsiella edwardsii*.

EXAMPLE 3

10 l of the culture medium described in Example 1 are sterilized in a fermenter and subsequently inoculated with 0.5 l of a 24-hour old culture of Serratia marcescens DSM 30126 as described in Example 1. The culture conditions are: 30° C., 600 rpm, 5 l of air/min. After 20 hours, 20 g of isoeugenol are added and the cultivation is continued. After 212 hours, the fermentation is stopped. The vanillin content in the culture broth is then 3.8 g/l, according to HPLC, corresponding to a yield of 20.5% of theory based on isoeugenol employed.

EXAMPLE 4

To a culture solution of Serratia marcescens DSM 30126 prepared as in Example 1 is added, as likewise described in Example 1, 2% by weight isoeugenol and 10% by weight Lewatit OC 1062 and it is incubated as likewise described in Example 1. After 12 days, the vanillin content of the culture broth is 2.5 g/l according to HPLC.

The fermentation broths obtained in Examples 1–4 are partially distilled with steam under atmospheric pressure in order to remove unreacted eugenol or isoeugenol. After cooling, the fermentation broth is extracted with a solvent which is immiscible with water, for example diisopropyl ether or ethyl acetate, until vanillin is no longer detectable in the aqueous phase. After the combined extracts have been dried, the solvent is removed. Kugelrohr distillation of the residue provides a crude vanillin with a purity > 95%. The crude vanillin obtained in this way can be purified even further by recrystallization from water.

What is claimed is:

1. A process for the preparation of vanillin which comprises oxidizing in a culture broth, 0.2 to 100 g/l of culture broth of eugenol, isoeugenol or a mixture of eugenol and isoeugenol microbially, in the presence of an effective amount of a microorganism selected from the genera Serratia, Klebsiella or Enterobacter, to form vanillin and isolating the vanillin which has formed from the culture broth.

2. The process of claim 1, wherein a strain of *Serratia ficaria, Serratia fonticola, Serratia liquefaciens, Serratia marcescens, Serratia marinorubra, Serratia odorifera, Serratia plymuthica, Serratia rubidaea, Enterobacter aerogenes, Enterobacter agglomerans, Enterobacter cloacae, Klebsiella aerogenes, Klebsiella pneumoniae* and *Klebsiella edwardsii* is used as the microorganism of the genera Serratia, Klebsiella or Enterobacter.

3. The process of claim 1, wherein an adsorbent is added to the culture broth.

4. The process of claim 3, wherein the adsorbent is active charcoal or an adsorber resin.

5. The process of claim 1, wherein the process is carried out at a temperature within the range from 10 to 45° C.

* * * * *